United States Patent [19]

Sherif et al.

[11] Patent Number: 5,142,078
[45] Date of Patent: Aug. 25, 1992

[54] ALUMINUM ALKOXIDE SYNTHESIS WITH TITANIUM AS A CATALYST

[75] Inventors: Fawzy G. Sherif, Stony Point; Johst H. Burk, Mohegan Lake, both of N.Y.

[73] Assignee: Akzo nv, Arnhem, Netherlands

[21] Appl. No.: 825,483

[22] Filed: Jan. 24, 1992

[51] Int. Cl.⁵ .................................. C07F 5/06
[52] U.S. Cl. ....................... 556/181; 556/179; 556/182
[58] Field of Search ............... 556/179, 181, 182; 505/1

[56] References Cited

U.S. PATENT DOCUMENTS

| | | | |
|---|---|---|---|
| 3,657,300 | 4/1972 | Beaver et al. | 556/181 |
| 3,720,698 | 3/1973 | Ichiki et al. | 556/181 X |
| 3,736,342 | 5/1973 | Ichiki et al. | 556/181 X |
| 4,764,357 | 8/1988 | Sherif et al. | 505/1 |

Primary Examiner—Arthur C. Prescott
Attorney, Agent, or Firm—Richard P. Fennelly; Louis A. Morris

[57] ABSTRACT

Aluminum alkoxides can be formed by reaction of aluminum metal and alcohol in the presence of soluble titanium (e.g., derived from a titanium carboxylate) as the catalyst for the reaction.

7 Claims, No Drawings

ALUMINUM ALKOXIDE SYNTHESIS WITH TITANIUM AS A CATALYST

BACKGROUND OF THE INVENTION

The synthesis of aluminum alkoxides from the metal using an alcohol reagent and catalyst is known with the following references illustrating various type of catalysts which might be used: U.S. Pat. Nos. 2,125,961 (use of iodine as a catalyst); 2,579,251 (use of anhydrous cupric chloride as a catalyst with the mention made of iodine, mercuric chloride, ferric chloride, stannic chloride, and boron trioxide as prior art catalysts); 2,636,865 (use of mercuric chloride as the catalyst); 2,666,076 (use of mercuric chloride, ferric chloride, stannic chloride, cupric chloride, boron trioxide, or iodine as the possible catalysts); and 4,745,204 (use of gallium and/or gallium based alloy). In all of these syntheses, the catalyst will reside with the product aluminum alkoxide as an impurity. This impurity will interfere with the utilization of aluminum alkoxide as a precursor for such final products as ultra pure ceramics for electronic applications and ultra pure alumina for laser grade powder.

SUMMARY OF THE INVENTION

The present invention resides in the use of soluble titanium as the catalyst for reaction of aluminum metal and alcohol. The titanium catalyst will not interfere with forming ultra pure alumina for electronic applications. In some instances titania is needed to form colored alumina crystals.

DETAILED DESCRIPTION OF THE INVENTION

The aluminum metal and alcohol reagent used in the present process is well known to persons of ordinary skill in the art from the foregoing U.S. patents, for example. Alkoxyalkanol reagents, e.g., 1-alkoxy-2-alkanol species such as 1-methoxy-2-propanol, are intended to be included in the definition of "alcohol" for purposes of this invention. The reagents are intended to be reacted in stoichiometric amount preferably under elevated temperature conditions.

In accordance with the present invention, a catalytically effective amount (e.g., from about $5 \times 10^{-3}$ mole to $2 \times 10^{-3}$ mole Ti per mole Al) as soluble titanium is used as the catalyst for the above-described reaction. The soluble titanium is supplied to the reaction medium by dissolving an alcohol-soluble titanium compound in the alcohol which serves as both reagent and, if liquid, as solvent for the reaction. Examples of suitable titanium compounds of this type include the titanium carboxylates which are titanium salts of long chain aliphatic or aromatic acids. A representative titanium compound of this type is titanium stearylate.

During the synthesis procedure of the present invention, aluminum metal reacts with the reagent alcohol and forms hydrogen. The hydrogen reduces the $Ti^{+4}$ catalyst to the blue $Ti^{+3}$ oxidation state. A few milligrams of unreacted aluminum metal in contact with a few grams of the formed alkoxide product will act as a catalyst for the following reactions without the need for additional titanium catalyst. This process can be practiced using a heel of material from the preceding reaction to make additional product. In each successive reaction step the impurity level will decrease.

In some cases, the aluminum alkoxide is needed as a starting material to prepare titanium sapphires ($Al_2O_3$:- $Ti^{+3}$), which are high purity crystals useful as tunable lasers and laser amplifiers which can be used at from 650 nm up to 1100 nm. The amount of titanium needed for the titanium sapphire enduse can be added initially to the reaction as $Ti^{+4}$. It is subsequently reduced in situ to $Ti^{+3}$, thus eliminating the handling of $Ti^{+3}$ in air and reducing the chances of oxidation of such a species to the undesirable $Ti^{+4}$ state.

The present invention is further understood by the Examples which follow.

EXAMPLE 1

Aluminum metal, 270 gms, 10 moles, was mixed with 2703.6 gms of 1-methoxy-2-propanol, 30 moles, in a 5 liter round bottom flask. The flask and all fittings were washed with a base, then an acid, deionized water, alcohol, acetone, then dried at 110° C. Titanium stearylate, 0.2 gms, was added to the mixture. The mixture was refluxed for two hours. After an induction period of two hours, hydrogen gas was evolved. The mixture was kept under a stream of dry, purified and filtered nitrogen gas. Hydrogen gas was released. After one more hour, the reaction was complete, and the solution became viscous with a bluish tint indicating $Ti^{+3}$. The viscous liquid was identified as aluminum tri-methoxy-propoxide. The aluminum content was found to be 8.85%, calculated for $Al(OC_4H_9O)_3 = 9.18\%$, indicating that the product is a 96.3% aluminum alkoxide in alcohol. Chemical analysis showed the following trace metals:

| | |
|---|---|
| Ti | 7.5 ppm |
| Fe | 7 ppb |
| Ca | <7 ppb |
| Cr | <12 ppb |
| Cu | <56 ppb |
| Ni | <63 ppb |

These trace metals are less than those in any aluminum alkoxide known. A commercial aluminum tri sec-butoxide contains 10.8 ppm Fe, 1 ppm Cr and <0.7 ppm Ca.

EXAMPLE 2

One tenth of the reaction mixture from Example containing a few grams of unreacted aluminum was blended with a mixture containing 135 gms aluminum and 1350 gms 1-methoxy-2-propanol and refluxed. After a two hour induction period, the reaction started without the need to add titanium catalyst. The heel from Example 1 acted as a catalyst. The amount of titanium in the heel corresponded to $2 \times 10^{-6}$ mole titanium per mole of aluminum in this reaction mixture.

EXAMPLE 3

The heel from Example 2 was used to start a reaction in this Example 3, similar to Example 2. The amount of titanium in the heel corresponded to $1 \times 10^{-7}$ mole titanium per mole of aluminum in this reaction mixture.

EXAMPLE 4

The heel from Example 3 was used to start a reaction in this Example 3, similar to Example 2. The amount of titanium in the heel corresponded to $5 \times 10^{-9}$ mole titanium per mole of aluminum in this reaction mixture.

COMPARATIVE EXAMPLE 5

This Example is similar to Example 1 except that no titanium catalyst was added. The alcohol was refluxed in contact with the aluminum metal for a period of twenty hours. No reaction occurred.

COMPARATIVE EXAMPLE 6

This Example illustrates that the titanium catalyst which activated the reaction between aluminum metal and alcohol did not activate the reaction between yttrium metal and alcohol.

In a one liter round bottom flask were mixed yttrium metal (44.5 gm, 0.5 mole) and 1-methoxy-3-propanol (270.3 gm, 3 moles). This mixture was refluxed under nitrogen gas after 0.2 gm of titanium stearylate had been added. No reaction took place even after eighteen hours of refluxing.

The foregoing Examples should not be construed in a limiting sense since they merely recite certain embodiments of the present invention. The scope of protection is set forth in the claims which follow.

I claim:

1. A process for forming an aluminum alkoxide by reaction of aluminum metal with an alcohol in the presence of soluble titanium as the catalyst for the reaction.

2. A process as claimed in claim 1 wherein the alcohol is an alkoxyalkanol.

3. A process as claimed in claim 1 wherein the soluble titanium is present at from about $5 \times 10^{-9}$ mole to $2 \times 10^{-3}$ mole titanium per mole aluminum.

4. A process as claimed in claim 2 wherein the soluble titanium is present at from about $5 \times 10^{-9}$ mole to $2 \times 10^{-3}$ mole titanium per mole aluminum.

5. A process as claimed in claim 1 wherein the soluble titanium is supplied as a titanium carboxylate.

6. A process as claimed in claim 2 wherein the soluble titanium is supplied as a titanium carboxylate.

7. A process as claimed in claim 3 wherein the soluble titanium is supplied as a titanium carboxylate.

* * * * *